United States Patent [19]

Hoback et al.

[11] Patent Number: 5,497,912
[45] Date of Patent: Mar. 12, 1996

[54] DISPOSABLE SELF-DISPENSING PRESSURIZED PACKAGE FOR DELIVERY OF STERILE FLUIDS

[76] Inventors: Michael W. Hoback, 5954 Pettus Rd., Antioch, Tenn. 37013; Walter C. Hennessee, 10002 Hogan Dr., Huntsville, Ala. 35803

[21] Appl. No.: 326,257

[22] Filed: Oct. 20, 1994

[51] Int. Cl.⁶ .................................. B65D 35/28
[52] U.S. Cl. .................... 222/95; 222/209; 222/386.5; 604/141
[58] Field of Search .................... 222/95, 386.5, 222/394, 401, 209; 604/141

[56] References Cited

U.S. PATENT DOCUMENTS

| | | | |
|---|---|---|---|
| 2,608,320 | 8/1952 | Harrison, Jr. | 222/95 |
| 3,838,794 | 10/1974 | Cogley et al. | 222/95 |
| 3,838,794 | 10/1974 | Cogley et al. | 222/95 |
| 3,949,753 | 4/1976 | Dockhorn | 222/95 X |
| 4,098,434 | 7/1978 | Uhlig | 222/209 x |
| 5,312,018 | 5/1994 | Evezich | 222/95 |

Primary Examiner—Gregory L. Huson
Attorney, Agent, or Firm—Rick R. Wascher

[57] ABSTRACT

The present invention is directed to a pressurized, disposable packaging system to dispense sterile fluids used in surgical procedures. The system consists of an inside, sealed bladder bag which contains the sterile fluid, and an outer bag which encloses, encapsulates and stabilizes the inner bag. The outer and inner bag share a common side seam. The outer pressure bag becomes air tight and sealed when connected to an external pressure device. The external pressure device causes pressure to be applied to an air space between the outer and the inner bag, thereby causing a force against the inner bag to expel the material through at least one exit port communicating the exterior of the outer bag to the interior of the inner bag. The outer bag also includes a pressure port for introducing pressurized gas or other fluid into the air space to force the sterile fluid within the inner bag out through the exit port.

23 Claims, 2 Drawing Sheets

DISPOSABLE SELF-DISPENSING PRESSURIZED PACKAGE FOR DELIVERY OF STERILE FLUIDS

BACKGROUND OF THE INVENTION

1. Field of the Invention

The present invention relates generally to devices, such as packages and bags, for dispensing sterile fluids, but more particularly to such devices capable of being including an interior bag and an exterior bag capable of being pressurized to force the fluid contents of the interior bag from an ejection port.

2. Description of the Related Art

In the majority of surgical procedures there is a requirement to have a pressurized flow of sterile fluids to the surgical site for the purpose of irrigation, hydrodissection, cavity distention, and lavage. Some examples of the surgical procedures requiring pressurized flow are laparoscopy, arthroscopy, cytoscopy, endoscopic sinus surgery, thoracoscopy, urethroscopy nephroscopy, hysteroscopy, and all open surgical procedures that require irrigation.

In the past, this pressurized fluid flow has been accomplished by various means. Perhaps the simplest of the various means entails hanging a sterile fluid bag from an intravenous (IV) pole. The system typically included a fluid delivery conduit (e.g., a length of tubing), attached to the bag and a fluid delivery instrument. The bag is then hung at an elevation greater than the instrument used to deliver or otherwise dispense the fluid to enable the force of gravity and the mass of the fluid to establish the pressurized fluid flow through the tubing. A common drawback associated with these type systems is the inability to maintain a constant delivery pressure. That is, as the fluid would be dispensed through the conduit and delivery instrument, the overall mass of the fluid would decrease and thus the pressurized flow due to the force of gravity would also decrease. In many such instances it was generally known that not all of the fluid inside the sterile bag was delivered to the desired site. Thus the only means to increase the fluid flow pressure and flow rate of the fluid was to raise the bag to a higher elevation. An example of one such sterile fluid bag that is commercially available is bag sold under the trademark VIAFLEX. VIAFLEX bags are constructed of a plastic material and contain various sterile fluid solutions for medical uses.

With the development of endoscopic and minimal invasion surgical procedures, such as percutaneous procedures, there exists a need to develop a more sophisticated system to deliver the fluid to the various instruments designed to accept the pressurized fluid flow in order to insure constant fluid delivery at a uniform pressure. As a result, medical and health care workers devised or implemented a way of attempting to solve the pressure delivery problems associated with gravitational delivery of sterile fluids. Their solution to the problem was to wrap a pressure cuff (e.g., common pressurizable blood pressure monitoring device) around a VIAFLEX type bag and apply squeeze pressure directly to the external surface of the bag. While this type of delivery enabled the user to administer fluids to the delivery site with much higher pressure than gravity alone could provide, it was difficult to maintain a constant pressure and dispense the entire fluid content of the bag.

A more sophisticated system was devised to replace the pressure cuff. The sophisticated system is capable of releasing fluid under pressure by a mechanical device whereby a VIAFLEX type fluid bag is placed into a box-like device capable of squeezing the bag via two opposing doors for applying pressure to the external surface of the bag. These systems are known to be expensive, cumbersome to set up, and still experience some of the limitations associated with emptying the entire contents of the bag because the mechanical compression of the bag could fold fluid pockets in the bag, thereby trapping sterile fluid inside the bag.

U.S. Pat. No. 3,838,794 granted to Cogley, et al is directed to a package for storing and dispensing liquids, and perhaps more importantly, for the reintroduction of fluids back into the Cogley device after it is emptied. The ability for reintroduction of fluids into such a device is believed to be an undesirable trait because of the inherent possibility of introducing contaminants with the replacement fluid reintroduced into the Cogley bag invention. The Cogley device incorporates a dual bag system where an interior fluid-containing bag is enclosed within an outer bag. The outer bag is configured to be pressurized and cause the interior fluid-containing bag to compress. The interior fluid-containing bag, as well as the outer bag, has an access port in which the interior bag may be punctured by a spike in the nature of a hollow piece of tubing or cannula with a pointed end such that the fluid can flow through the tubing.

The Cogley invention provides lateral ribs for rigidity in order that his device does not trap fluid within the bag when the bag invention is nearly empty. The lateral ribs are applied to the inner bag component and enable the inner bag to maintain a substantially upright relationship with respect to the outer bag component. The Cogley device, therefore, is believed to be capable of dispensing the entire content of the inner bag by virtue of the lateral rib arrangement. The ribs, however, are believed to add considerable cost, among other things, to the manufacture of the Cogley invention when one considers the present cost of manufacturing a sterile fluid bag.

The Cogley bag does not provide a suitable means for even application of pressure to the bag surface and thus a consistent delivery of fluid at a relatively constant pressure is believed to unobtainable to a large degree with the Cogley device. For example, while the inner bag of the Cogley device might be stabilized vertically, its relative position is not always centered in the outer bag. Thus pressure introduced into the outer bag may apply and uneven fluid delivery pressure force to the from or the back of the bag and not necessarily uniform. Such uneven application of pressure is believed to affect the delivery of the fluid from the inner bag. A stabilized inner bag, if properly constructed, would be capable of administering the entire content of the fluid within the bag, and enable a constant uniform pressure to the front and back surfaces of the inner bag to drive the delivery of the fluid, as well as prevent the reintroduction of fluid to eliminate the possibility of introducing invisible contaminants bag into the inner bag. In addition, the Cogley device is believed to provide an ineffectual uniform sterile seal between the inner and outer bags because of the inherent ability of the inner bag to flop around inside of the outer bag prior to, during, and even after delivery of the fluid from the inner bag.

Accordingly, until now, a pressurized fluid flow bag having an exterior bag and a stabilized interior bag, enabling the fluid delivery pressure force to be more uniformly equalized over the entire surface of the inner bag and thus more evenly and efficiently distribute the fluid contained within the interior bag under a constant pressure has not been invented.

SUMMARY OF THE INVENTION

An embodiment of the present invention is directed to a disposable package consisting of a flexible sealed inner bladder bag which contains a sterile surgical fluid and at least one, but preferably two, access ports communicating the interior of the bag with the environment. In the preferred embodiment, one port permits a standard sterile IV tubing set to spike, or puncture a port seal, and allow the fluid to flow from the inner bag through the IV tubing and into a surgical instrument designed to attach to the IV tubing set and use pressurized fluid flow. A second port, commonly referred to as a "MEDS" port provides access to the inner bladder bag for the addition of other or additional sterile fluids, or medication additives.

This inner bladder bag is preferably contained in, encapsulated and stabilized by, an outer flexible bag which is larger than the inner bag. An air space is established between the inner and outer bags allowing the outer bag, via the air space, to accept a pressurized gas (such as carbon dioxide) or air from an external air pressure introduction source.

The air pressure introduction source connects to a port which provides access to the space between the two bags. When gas pressure is introduced into the space between the two bags, the gas pressure applies a force substantially evenly to the outer surface of the inner bag. The substantially even application of pressure drives the sterile fluid contained within the inner bladder bag out through the spike port under pressure proportional to the pressure force generated in the space between the two bags and applied to the outer surface of the inner bag. The common seam between the inner and outer bag insures uniform and thorough delivery of the sterile fluid. The pressure generated in the space between the two bags can be monitored by an optional pressure gauge.

In addition, if one were to puncture the outer bag to pressurize it and the inner bag was not stabilized within the outer bag, the inner bag may overlie the site of the pressure puncture and be inadvertently punctured with the outer bag. Thus, the inadvertent rupture of the inner bag would introduce contaminants and allow the sterile fluid to seep from the pressure hole created in the outer bag.

The present invention comprises an apparatus, system and method of making the apparatus. Accordingly, the invention can be summarized in a variety of ways, one of which is the following: a sterile fluid storage bag comprising: a flexible outer bag having an interior, an exterior exposed to atmosphere, and a first edge; a flexible inner bag having an interior capable of receiving a sterile fluid, an exterior, and a second edge; a seam joining the first edge and the second edge; an air space between the interior of the outer bag and the exterior of the inner bag; at least one fluid flow port communicating the exterior of the outer bag with the interior of the inner bag; and at least one pressure port communicating the exterior of the outer bag and the air space enabling the air space to be pressurized.

The sterile fluid bag system may also include pressure means for introducing gaseous pressure into the air space or pressure gauge means for monitoring the pressure introduced into the air space. The at least one pressure port may include a one-way valve allowing pressure to be introduced into the air space and preventing the escape of air pressure from the air space. The at least one fluid flow port and the at least one pressure port may include a spike port and an injection port. A one-way valve means may be interconnected between the pressure means and the air space for preventing backflow of pressure from the air space to the pressure means, and a hanger means may be attached to the outer bag for hanging the sterile fluid storage bag. A stay means may be provided for holding the spike port and the injection port in proper operative alignment with the outer bag.

The invention may also be summarized as follows: a sterile fluid storage bag, comprising: an inner bag having an interior for containing a sterile fluid and having a side seam; an outer bag having a side seam; a weld joining the side seam of the inner bag to the side seam of the outer bag establishing an air space between the inner bag and outer bag and stabilizing the inner bag with respect to the outer bag; pressure means for introducing gaseous pressure into the air space; and fluid flow means for injecting and ejecting fluid from the interior of the inner bag.

Yet another way of summarizing the present invention is: a bag for storing and dispensing sterile fluids, comprising: a first fluid reservoir formed by the edge of first fluid container having an interior and an exterior wherein the edge includes a top portion, a bottom portion and side portions; a second fluid reservoir formed by the edge of a second fluid container having an interior and an exterior wherein the edge includes a top portion, a bottom portion and side portions; a heat seal joining the side edge portions of the first fluid container and the side edge portions of the second fluid container; an air space between the exterior of the first fluid container and the interior of the second fluid container; at least one fluid flow port providing flow communication between the interior of the first container with the atmosphere; and at least one pressure port communicating the exterior of the second fluid container with the air space enabling the air space to be pressurized.

The inventive method may be summarized as follows: a method of making a sterile fluid storage bag, comprising the steps of: providing a first bag having an interior for containing a sterile fluid and having a side seam; providing a second bag having an interior and a side seam; positioning the first bag in the interior of the second bag; joining the side seam of the first bag to the side seam of the second bag and establishing an air space between the first bag and the second bag; providing a fluid exit port and a gaseous entry port enabling the air space to be pressurized through the gaseous entry port and enabling sterile fluid to be dispensed from the first bag.

The method may also be summarized as follows: a method of making a sterile fluid storage bag, comprising the steps of: providing a sheet of elastomeric material having a top, a bottom, and spaced apart side edges; folding the elastomeric material onto itself to form a first pocket; folding the folded elastomeric material of the preceding step onto itself to form a second pocket having a top, a bottom, and spaced apart sides enabling the second pocket to engulf the first pocket having a top, a bottom and spaced apart sides; and joining the spaced apart sides of the first pocket to the spaced apart sides of the second pocket and joining the bottom of the first pocket to the bottom of the second pocket. The method step of joining comprises sealing the pockets, and the sealing may include heat welding.

The first folding step may include folding the bottom of the elastomeric material onto the top of the elastomeric material. The method may also include the step of providing at least on fluid flow port and positioning the at least one fluid flow port between the pockets prior to the joining step.

It is an object of the present invention to provide an economical, easy to use, and simple system for the administering of sterile surgical fluids under pressure to surgical instruments designed to accept connection to these type fluid bags.

DETAILED DESCRIPTION OF THE PREFERRED EMBODIMENT(S)

Figure 1:
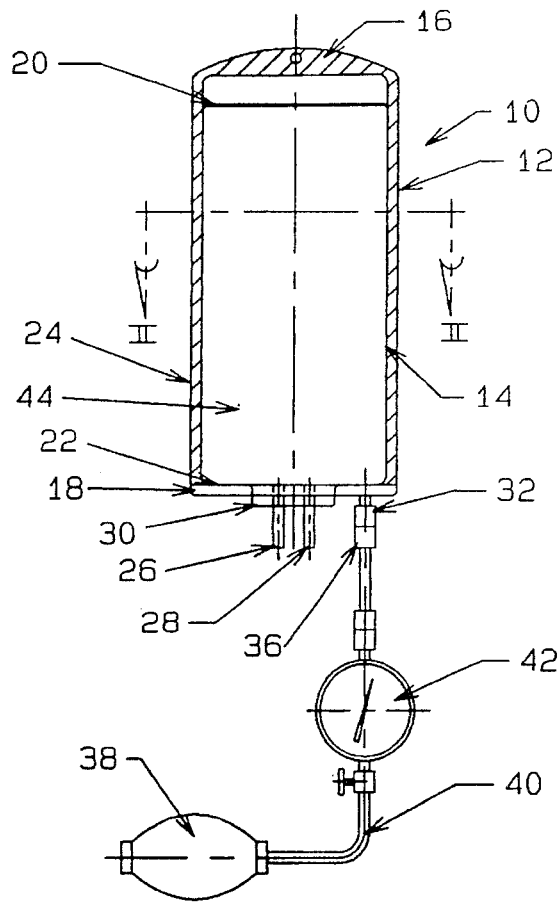
FIG. 1 is a side view of an embodiment of the bag of the present invention shown with a pressure regulating mechanism attached thereto.
Figure 2:
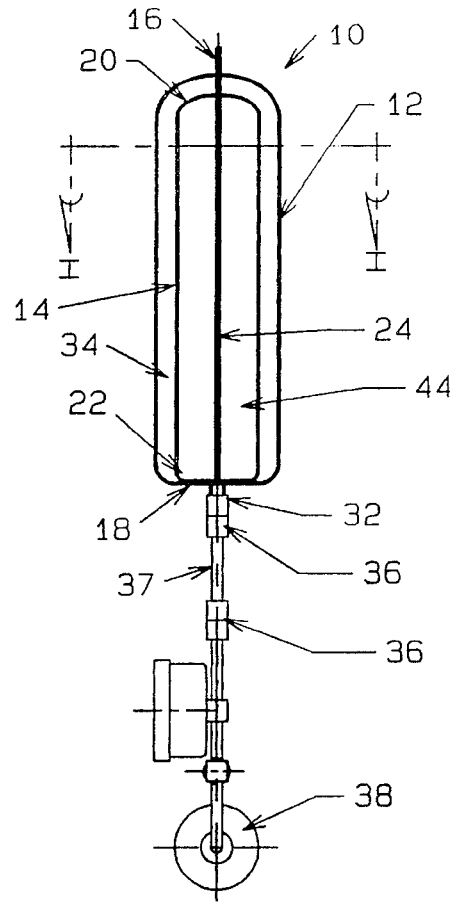
FIG. 2 is a front partially cross-sectional view of the embodiment of the invention shown in FIG. 1.

With reference to FIGS. 1 and 2, an embodiment of the invention is designated generally by the reference numeral 10. Embodiment 10 incorporates an outer bag 12 and an inner bag 14. The outer bag has a top 16 and a bottom 18. Similarly, the inner bag has a top 20 and a bottom 22. Each bag has a common side seam 24. The side seams of each bag are joined at a single heat seal or weld in order to maintain the inner bag 14 in an operable stabilized alignment with the outer bag 12.

The common seam 24 is particularly important and useful when the outer bag is pressurized, as will be described hereinbelow, the inner bag maintains its relative alignment with the outer bag and therefore does not crumple and trap sterile fluid within the folds of the inner bag thereby creating waste. It also enables a constant uniform force to be applied to the outer surface of the inner bladder bag, and provide the user with a visual determination of the volume content of the inner bag, thereby enabling the user to accurately determine when a replacement bag is necessary.

An injection port 26 and spike port 28 are formed at the bottom 18 and 22 of the bags 12 and 14. The ports preferably have a rigid or semi-rigid stay 30 which serves as the means of connection of the ports to the bags as shown in FIG. 2. The stay 30 enables the ports 26 and 28 to maintain proper alignment with the bag to enable the fluid contents to be evenly distributed and dispersed therefrom. Absent the stay component, the ports could be bent in such a fashion that the central aperture (not shown) by having either the outer or inner bag fold over the port thereby sealing off or in some way restricting the delivery of the fluid contained within the inner bag.

Pressure port 32 is positioned at the bottom 18 of the outer bag 12. The pressure port forms a communication between the exterior of the outer bag and its interior pressurizing air space 34. High pressure luar lock 36 is in line with the pressure port 32 to set up a one-way flow such that the pressure introduced through the one way pressurizing bulb 38 of the pressure bulb assembly 40 is prevented from reverse flow thereby trapping the pressurized air within the air space 34. A conventional crimping device 37 may also be used in order that dual luar locks 36 (FIG. 1) may be incorporated into the inventive system. The crimper 37 would prevent backflow of the fluid toward the pressure bulb 38. A pressure gauge 42 is preferably positioned in line with the port 32 and pressure bulb assembly 40 to enable the user to accurately monitor the pressure within the air space 34 between the outer bag 12 and the inner bag 14. Of course, alternate embodiments of the invention may also incorporate one way valves to prevent backflow of fluid in undesired directions.

Of course, the pressure bulb assembly 40 and pressure gauge 42 can be replaced by any suitable means of introducing and monitoring the pressure within the air space 34. An example of such an alternate embodiment which is not shown but found in the industry, is an automatic pressure pump which maintains a pre-set pressure level within the air space 34 between the outer and inner bags, 12 and 14 respectively. The automated device essentially eliminates manual pressurization of the bag. In this fashion, as the fluid 44 within the inner bag 14 is expelled through the port 28, and therefore allows the air space 34 to increase in volume causing the pressure within the bag to drop. The user may manually pump the bulb 38 to reintroduce pressure to reestablish the desired pressure level or the automated device, as mentioned, can account for the increased volume to add additional air or carbon dioxide to the air space 34 to maintain the desired pressure level.

Figure 3:
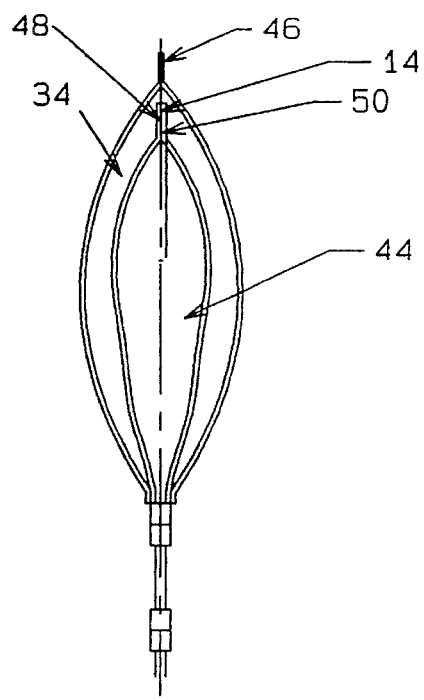
FIG. 3 is a side cross-sectional view of an embodiment of the present invention shown in operable vertical alignment with the inner bag approximately half full of sterile fluid.
Figure 4:
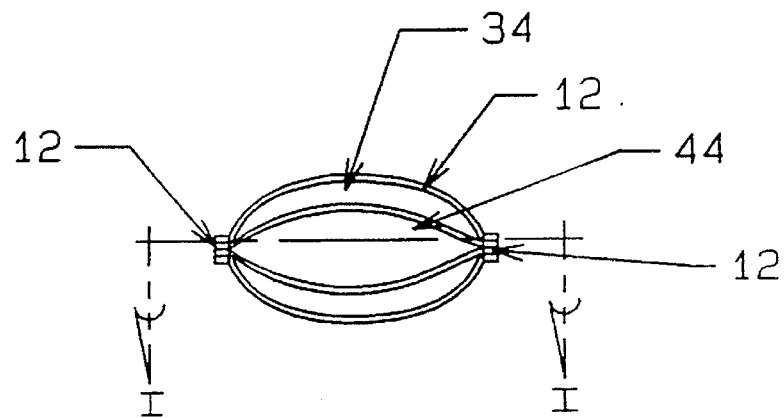
FIG. 4 is a top cross-sectional view taken along line I—I of FIG. 1.

With reference to FIGS. 3 and 4, the preferred embodiment of the invention is shown first in operable alignment in FIG. 3, and then in inverted alignment in FIG. 4. Hanger 46 is provided to enable the entire inventive assembly to hang freely from an IV pole or the like. FIGS. 3 and 4 are partially cross-sectional and thus do not easily show the common seam illustrated in FIGS. 1, 2 and 5 described below.

As illustrated in FIGS. 3 and 4, the fluid 44 has a tendency to gravitate depending upon the position or orientation of the bag. The inner bag 14 therefore has a tendency to collapse in response to gravity as well as the pressure introduced into the air space 34.

Figure 5:
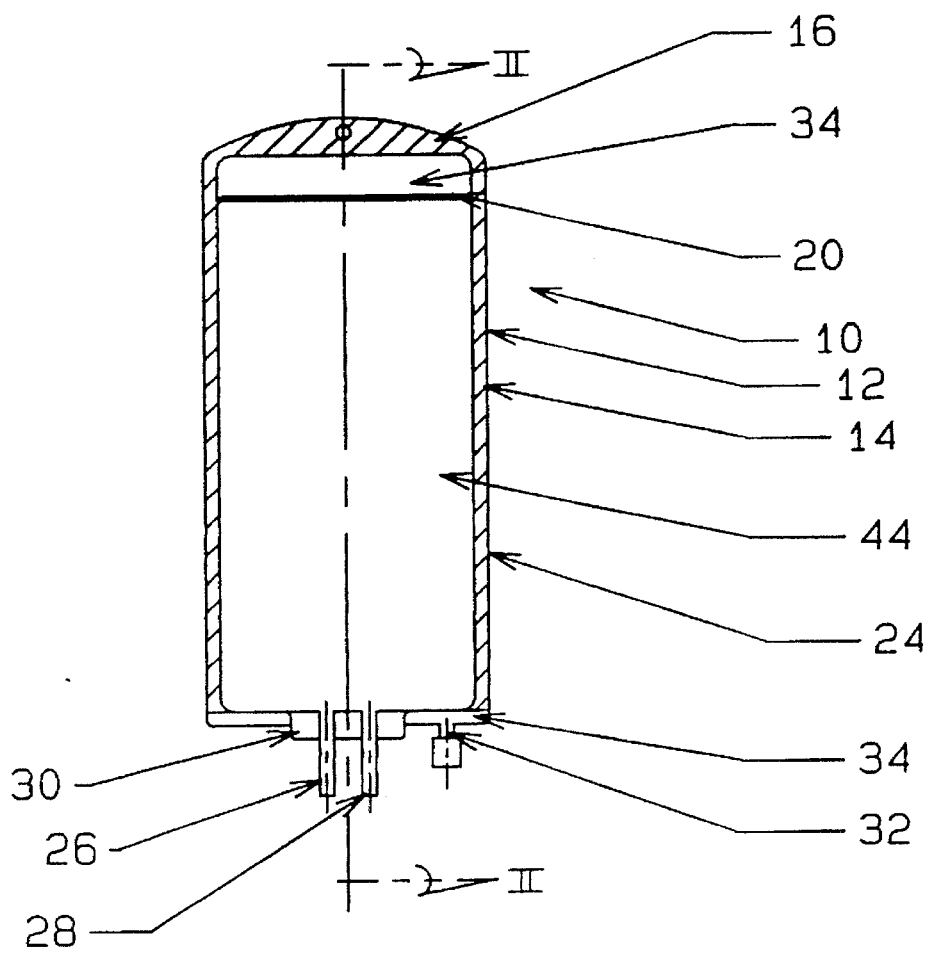
FIG. 5 is a top cross-sectional view taken along line II—II of FIG. 2.

With reference to FIG. 5, the embodiment of the invention shown in FIG. 1 is illustrated in an inverted arrangement. In this Figure, the interior bag 14 is full of fluid 44 and thus is shown without a collapsing contact between the surfaces of the bag 48 and 50 (see also FIGS. 3 and 4).

These and other embodiments of the present invention shall become apparent after consideration of the specifications, drawings and claims appended hereto. All such equivalents and alternate embodiments are contemplated by the scope of the present invention whose only limitation is the scope of the appended claims.

What is claimed is:

1. A pressurized sterile fluid storage bag having a top and a bottom comprising:

a flexible outer bag having an interior, an exterior exposed to atmosphere, and a first edge located at a side other than a bottom of the outer bag;

a flexible inner bag having an interior capable of receiving a sterile fluid, an exterior, and a second edge located at a side other than a bottom of the inner bag;

a seam joining at least a portion of the first edge and at least a portion of the second edge enabling the inner bag to remain oriented parallel and positionally fixed with respect to the outer bag throughout the useful life of the sterile fluid storage bag and further permitting the sterile fluid within the inner bag to move and collect at a bottom of the inner bag in response to the force of gravity when the storage bag is held supported at the top and preventing sterile fluid from being trapped within the inner bag as the sterile fluid is dispensed therefrom;

an air space between the interior of the outer bag and the exterior of the inner bag;

at least one fluid flow port communicating the exterior of the outer bag with the interior of the inner bag; and at least one pressure port communicating the exterior of the outer bag and the air space enabling the air space to be pressurized.

2. The sterile fluid storage bag of claim 1, further comprising:

pressure means for introducing gaseous pressure into the air space.

3. The sterile fluid storage bag of claim 1, wherein:

the at least one pressure port includes a one-way valve allowing pressure to be introduced into the air space and preventing the escape of air pressure from the air space.

4. The sterile fluid storage bag of claim 2, further including:

pressure gauge means for monitoring the pressure introduced into the air space.

5. The sterile fluid storage bag of claim 1, wherein the at least one fluid flow port and the at least one pressure port includes:

a spike port and an injection port.

6. The sterile fluid storage bag of claim 2, further including:

one-way valve means interconnected between the pressure means and the air space for preventing backflow of pressure from the air space to the pressure means.

7. The invention of claim 1, further including:

hanger means attached to the outer bag for hanging the sterile fluid storage bag.

8. The invention of claim 5, further including:

stay means for holding the spike port and the injection port in proper operative alignment with the outer bag.

9. A sterile fluid storage bag having a top and a bottom, comprising:

an inner bag having an interior for containing a sterile fluid and having a side seam in addition to a bottom;

an outer bag having a side seam in addition to a bottom;

a weld joining at least a portion of the side seam of the inner bag to at least a portion of the side seam of the outer bag establishing an air space between the inner bag and outer bag and stabilizing the inner bag with respect to the outer bag in a manner such that the inner bag remains oriented parallel and positionally fixed with respect to the outer bag throughout the useful sterile fluid storage bag and further permitting the sterile fluid within the inner bag to move and collect at the bottom of the inner bag in response to the force of gravity when the storage bag is held supported at the top and preventing sterile fluid from being trapped within the inner bag as the sterile fluid is dispensed therefrom;

pressure means for introducing gaseous pressure into the air space; and fluid flow means for injecting and ejecting fluid from the interior of the inner bag.

10. The sterile fluid storage bag of claim 9, wherein the pressure means further comprises:

at least one pressure port allowing one-way introduction into the air space and preventing the escape of air pressure from the air space.

11. The sterile fluid storage bag of claim 10, further including:

pressure gauge means for monitoring the pressure introduced into the air space.

12. The sterile fluid storage bag of claim 1, wherein the at least one pressure port includes:

an injection port.

13. The sterile fluid storage bag of claim 9, wherein the fluid flow means further comprises:

at least one spike port.

14. The sterile fluid flow bag of claim 13, wherein the fluid flow means further includes one-way valve means for preventing backflow of fluid into the inner bag.

15. The sterile fluid storage bag of claim 9, further including:

hanger means attached to the outer bag for hanging the sterile fluid storage bag from an IV pole.

16. The sterile fluid storage bag of claim 9, further including:

stay means for holding the pressure means and fluid flow means in proper operative alignment with the outer bag.

17. A bag for storing and dispensing sterile fluids, the bag having a top, a bottom, and further comprising:

a first fluid reservoir formed by the edge of a first fluid container having an interior and an exterior wherein the edge includes a bottom portion and side portions;

a second fluid reservoir formed by the edge of a second fluid container having an interior and an exterior wherein the edge includes a bottom portion and side portions;

a heat seal joining at least a portion of the side portions of the first fluid container with at least a portion of the side portions of the second fluid container in a manner such that the first fluid container remains oriented parallel and positionally fixed with respect to the second fluid container throughout the useful life of the bag and further permitting a sterile fluid within the first fluid reservoir to move and collect at the bottom of the first fluid reservoir in response to the force of gravity when the bag is held supported at the top and preventing the sterile fluid from being trapped within the first fluid container as the sterile fluid is dispensed from it and the first fluid container collapses;

an air space between the exterior of the first fluid container and the interior of the second fluid container;

at least one fluid flow port providing flow communication between the interior of the first container with the atmosphere; and at least one pressure port communicating the exterior of the second fluid container with the air space enabling the air space to be pressurized.

18. The bag of claim 17, further comprising:

pressurizing means for introducing gaseous fluid pressure into the air space.

19. The sterile fluid storage bag of claim 17, wherein:

the at least one pressure port includes a one-way valve allowing pressure to be introduced into the air space and preventing the escape of air pressure from the air space.

20. The sterile fluid storage bag of claim 18, further including:

pressure gauge means for monitoring the pressure introduced into the air space.

21. The sterile fluid storage bag of claim 17, wherein the at least one fluid flow port and the at least one pressure port includes:

a spike port and an injection port respectively.

22. The invention of claim 17, further including:

hanger means attached to the second fluid container for hanging the combination of the first and second fluid containers from an IV pole.

23. The invention of claim 21, further including:

stay means for holding the spike port and the injection port in proper operative alignment with the bag.

* * * * *